US012622631B2

(12) United States Patent
Al-Louzi et al.

(10) Patent No.: US 12,622,631 B2
(45) Date of Patent: May 12, 2026

(54) SYSTEMS AND METHODS FOR QUANTIFYING RETROGRADE TRANS-SYNAPTIC DEGENERATION

(71) Applicant: Cedars-Sinai Medical Center, Los Angeles, CA (US)

(72) Inventors: Omar Al-Louzi, Los Angeles, CA (US); Pascal Sati, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 18/641,404

(22) Filed: Apr. 21, 2024

(65) Prior Publication Data

US 2024/0350074 A1 Oct. 24, 2024

Related U.S. Application Data

(60) Provisional application No. 63/497,698, filed on Apr. 21, 2023.

(51) Int. Cl.
A61B 5/00 (2006.01)
A61B 3/00 (2006.01)
(Continued)

(52) U.S. Cl.
CPC .......... A61B 5/4064 (2013.01); A61B 3/0025 (2013.01); A61B 3/1005 (2013.01);
(Continued)

(58) Field of Classification Search
CPC ... A61B 5/4064; A61B 3/0025; A61B 3/1005; A61B 3/102; A61B 3/1225;
(Continued)

(56) References Cited

U.S. PATENT DOCUMENTS

2009/0123044 A1* 5/2009 Huang ................. A61B 3/0058
382/128
2014/0218686 A1* 8/2014 Reisman ............... G06T 7/0012
351/246
(Continued)

OTHER PUBLICATIONS

Ababneh N, Alshaer W, Al-Louzi O, et al. In vitro selection of modified RNA aptamers against CD44 cancer stem cell marker. Nucleic Acid Ther. 2013;23(6):401-407.
(Continued)

*Primary Examiner* — Baisakhi Roy
(74) *Attorney, Agent, or Firm* — Nixon Peabody LLP

(57) ABSTRACT
A method for quantifying retrograde trans-synaptic degeneration (rTSD) in a patient includes receiving optical coherence tomography (OCT) image data associated with a left retina and a right retina of the patient. The method further includes analyzing the OCT image data to determine a thickness of one or more retinal layers of the left retina and one or more retinal layers of the right retina. The method further includes, based at least in part on the determined thicknesses, determining a value of an rTSD index that is indicative of a level of rTSD in the patient. The rTSD index can be based at least in part on the thicknesses of retinal layers connected to a left optic radiation of the patient versus the thicknesses of retinal layers connected to a right optic radiation of the patient.

20 Claims, 7 Drawing Sheets

—200

202 — Receive OCT image data associated with left retina and right retina

204 — Analyze the OCT image data to determine the thickness of retina layers of the left retina and the right retina 206 — Determine rTSD index value based on thickness of retinal layers of the left retina and right retina

(51) Int. Cl.
| | |
|---|---|
| *A61B 3/10* | (2006.01) |
| *A61B 3/12* | (2006.01) |
| *G16H 50/30* | (2018.01) |

(52) U.S. Cl.
CPC ............ *A61B 3/102* (2013.01); *A61B 3/1225* (2013.01); *A61B 5/7278* (2013.01); *G16H 50/30* (2018.01)

(58) Field of Classification Search
CPC ..... A61B 5/7278; A61B 5/0066; A61B 5/055; A61B 5/4088; A61B 5/4842
See application file for complete search history.

(56) References Cited

U.S. PATENT DOCUMENTS

| | | | | |
|---|---|---|---|---|
| 2014/0327916 A1* | 11/2014 | Inoue | ...................... | A61B 3/102 |
| | | | | 356/479 |
| 2015/0103314 A1* | 4/2015 | Pujol Ramo | ........... | A61B 3/028 |
| | | | | 351/246 |
| 2016/0300352 A1* | 10/2016 | Raj | ....................... | G06V 10/764 |
| 2018/0064335 A1* | 3/2018 | Rutschman | ............ | A61B 3/145 |
| 2022/0192484 A1* | 6/2022 | Donahue | .............. | A61B 3/1005 |
| 2023/0050186 A1* | 2/2023 | Rotenstreich | ........ | A61B 5/7267 |
| 2024/0415983 A1* | 12/2024 | Boye | ....................... | C07K 14/47 |

OTHER PUBLICATIONS

Al-Louzi O, Saidha S, Ratchford JN, et al. Optical coherence tomography reflects brain atrophy in MS: A four year study. Ann Neurol. Published online Jul. 18, 2015.

Al-Louzi OA, Bhargava P, Newsome SD, et al. Outer retinal changes following acute optic neuritis. Mult Scler J. 2016;22(3):362-372.

Al-Louzi O, Button J, Newsome SD, Calabresi PA, Saidha S. Retrograde trans-synaptic visual pathway degeneration in multiple sclerosis: A case series. Mult Scler. 2017;23(7):1035-1039.

Al-Louzi O, Sotirchos ES, Vidal-Jordana A, et al. Characteristics of morphologic macular abnormalities in neuroimmunology practice. Mult Scler J. 2019;25(3):361-371.

Al-Louzi O, Roy S, Osuorah I, et al. Progressive multifocal leukoencephalopathy lesion and brain parenchymal segmentation from MRI using serial deep convolutional neural networks. NeuroImage Clin. 2020;28:102499.

Cortese I, Beck ES, Al-Louzi O, et al. BK virus-specific T cells for immunotherapy of progressive multifocal leukoencephalopathy: an open-label, single-cohort pilot study. Lancet Neurol. 2021;20(8):639-652.

Sati P, Thomasson DM, Li N, et al. Rapid, high-resolution, whole-brain, susceptibility-based MRI of multiple sclerosis. Mult Scler. 2014;20(11):1464-1470.

La Rosa F, Wynen M, Al-Louzi O, et al. Cortical lesions, central vein sign, and paramagnetic rim lesions in multiple sclerosis: emerging machine learning techniques and future avenues. Published online Jan. 19, 2022.

Bazin PL, Ye C, Bogovic JA, et al. Direct segmentation of the major white matter tracts in diffusion tensor images. Neuroimage. 2011;58(2):458-468.

Huo Y, Plassard AJ, Carass A, et al. Consistent cortical reconstruction and multi-atlas brain segmentation. Neuroimage. 2016;138:197-210.

Reich DS, Lucchinetti CF, Calabresi PA. Multiple Sclerosis. Longo DL, ed. N Engl J Med. 2018;378(2):169-180.

Manouchehri N, Stüve O. Should ocrelizumab be used in non-active primary progressive multiple sclerosis? Time for a re-assessment. Ther Adv Neurol Disord. 2021;14:1756286421990500.

Simpson A, Mowry EM, Newsome SD. Early Aggressive Treatment Approaches for Multiple Sclerosis. Curr Treat Options Neurol 2021 237. 2021;23(7):1-21.

Trapp BD, Peterson J, Ransohoff RM, Rudick R, Mörk S, Bö L. Axonal transection in the lesions of multiple sclerosis. N Engl J Med. 1998;338(5):278-285.

Kappos L, Wolinsky JS, Giovannoni G, et al. Contribution of Relapse-Independent Progression vs Relapse-Associated Worsening to Overall Confirmed Disability Accumulation in Typical Relapsing Multiple Sclerosis in a Pooled Analysis of 2 Randomized Clinical Trials. JAMA Neurol. 2020;77(9):1132-1140.

Galetta KM, Calabresi P a, Frohman EM, Balcer LJ. Optical coherence tomography (OCT): imaging the visual pathway as a model for neurodegeneration. Neurotherapeutics. 2011;8(1):117-132.

Balk LJ, Steenwijk MD, Tewarie P, et al. Bidirectional trans-synaptic axonal degeneration in the visual pathway in multiple sclerosis. J Neurol Neurosurg Psychiatry. 2015;86(4):419-424.

Keller J, Sánchez-Dalmau BF, Villoslada P. Lesions in the posterior visual pathway promote trans-synaptic degeneration of retinal ganglion cells. PLoS One. 2014;9(5):e97444.

Klistorner A, Sriram P, Vootakuru N, et al. Axonal loss of retinal neurons in multiple sclerosis associated with optic radiation lesions. Neurology. 2014;82:2165-2172.

Treaba CA, Conti A, Klawiter EC, et al. Cortical and phase rim lesions on 7 T MRI as markers of multiple sclerosis disease progression. Brain Commun. 2021;3(3).

Marcille M, Hurtado Rúa S, Tyshkov C, et al. Disease correlates of rim lesions on quantitative susceptibility mapping in multiple sclerosis. Sci Reports 2022 121. 2022; 12(1):1-10.

Wallin MT, Culpepper WJ, Campbell JD, et al. The prevalence of MS in the United States: A population-based estimate using health claims data. Neurology. 2019;92(10):E1029-E1040.

Hartung DM. Economics and Cost-Effectiveness of Multiple Sclerosis Therapies in the USA. Neurotherapeutics. 2017;14(4):1018-1026.

Bebo B, Cintina I, LaRocca N, et al. The Economic Burden of Multiple Sclerosis in the United States. Neurology. 2022;98(18):e1810-e1817.

Heesen C, Böhm J, Reich C, Kasper J, Goebel M, Gold SM. Patient perception of bodily functions in multiple sclerosis: Gait and visual function are the most valuable. Mult Scler. 2008;14(7):988-991.

Lublin FD, Reingold SC, Cohen JA, et al. Defining the clinical course of multiple sclerosis: The 2013 revisions. Neurology. 2014;83(3):278.

Rovaris M, Confavreux C, Furlan R, Kappos L, Comi G, Filippi M. Secondary progressive multiple sclerosis: current knowledge and future challenges. Lancet Neurol. 2006;5(4):343-354.

Koch M, Kingwell E, Rieckmann P, et al. The natural history of secondary progressive multiple sclerosis. J Neurol Neurosurg Psychiatry. 2010;81(9):1039-1043.

Scalfari A, Neuhaus A, Daumer M, Muraro PA, Ebers GC. Onset of secondary progressive phase and long-term evolution of multiple sclerosis. J Neurol Neurosurg Psychiatry. 2014,85(1):67-75.

Correale J, Gaitán MI, Ysrraelit MC, Fiol MP. Progressive multiple sclerosis: from pathogenic mechanisms to treatment. Brain. 2017;140(3):527-546.

Ziemssen T, Tolley C, Bennett B, et al. A mixed methods approach towards understanding key disease characteristics associated with the progression from RRMS to SPMS: Physicians' and patients' views. Mult Scler Relat Disord. 2020;38:101861.

Deleglise B, Magnifico S, Duplus E, et al. β-amyloid induces a dying-back process and remote trans-synaptic alterations in a microfluidic-based reconstructed neuronal network. Acta Neuropathol Commun. 2014;2(1).

Braak H, Del Tredici K. Alzheimer's pathogenesis: is there neuron-to-neuron propagation? Acta Neuropathol. 2011;121(5):589-595.

Ferreira N, Gonçalves NP, Jan A, et al. Trans-synaptic spreading of alpha-synuclein pathology through sensory afferents leads to sensory nerve degeneration and neuropathic pain. Acta Neuropathol Commun. 2021;9(1):1-17.

Fogarty M. Amyotrophic lateral sclerosis as a synaptopathy. Neural Regen Res. 2019;14(2):189.

Al-Louzi O, Prasad S, Mallery RM. Utility of optical coherence tomography in the evaluation of sellar and parasellar mass lesions. Curr Opin Endocrinol Diabetes Obes. 2018;25(4):274-284.

(56)          References Cited

OTHER PUBLICATIONS

Caldito NG, Saidha S, Sotirchos ES, Al-Louzi O, et al. Brain and retinal atrophy in African-Americans versus Caucasian-Americans with multiple sclerosis: a longitudinal study. Brain. 2018;141(11):3115-3129.

Kimbrough DJ, Sotirchos ES, Wilson JA, Al-Louzi O, et al. Retinal Damage and Vision Loss in African-American Multiple Sclerosis Patients. Ann Neurol. Published online Nov. 8, 2014.

Walter SD, Ishikawa H, Galetta KM, et al. Ganglion cell loss in relation to visual disability in multiple sclerosis. Ophthalmology. 2012;119(6):1250-1257.

Lambe J, Fitzgerald KC, Murphy OC, et al. Association of Spectral-Domain OCT With Long-term Disability Worsening in Multiple Sclerosis. Neurology. 2021;96(16):e2058-e2069.

Minneboo A, Uitdehaag B, Jongen P, et al. Association between MRI parameters and the MS severity scale: a 12 year follow-up study: http://dx.doi.org/101177/1352458509102617. 2009;15(5):632-637.

Sati P, Oh J, Constable RT, et al. The central vein sign and its clinical evaluation for the diagnosis of multiple sclerosis: a consensus statement from the North American Imaging in Multiple Sclerosis Cooperative. Nat Rev Neurol. 2016;12(12):714-722.

Tallantyre EC, Dixon JE, Donaldson I, et al. Ultra-high-field imaging distinguishes MS lesions from asymptomatic white matter lesions. Neurology. 2011;76(6):534-539.

Solomon AJ, Watts R, Ontaneda D, Absinta M, Sati P, Reich DS. Diagnostic performance of central vein sign for multiple sclerosis with a simplified three-lesion algorithm. Mult Scler J. 2018;24(6):750-757.

Maggi P, Absinta M, Grammatico M, et al. Central vein sign differentiates Multiple Sclerosis from central nervous system inflammatory vasculopathies. Ann Neurol. 2018;83(2):283-294.

Tan IL, Van Schijndel RA, Pouwels PJW, et al. MR Venography of Multiple Sclerosis. AJNR Am J Neuroradiol. 2000;21(6):1039. /pmc/articles/PMC7973892/. Accessed Nov. 27, 2021.

Castellaro M, Tamanti A, Pisani Al, Pizzini FB, Crescenzo F, Calabrese M. The Use of the Central Vein Sign in the Diagnosis of Multiple Sclerosis: A Systematic Review and Meta-analysis. Diagnostics. 67. 2020;10(12):1025.

Lucchinetti C, Brück W, Parisi J, Scheithauer B, Rodriguez M, Lassmann H. Heterogeneity of multiple sclerosis lesions: Implications for the pathogenesis of demyelination. Ann Neurol. 2000;47(6):707-717.

Frischer JM, Bramow S, Dal-Bianco A, et al. The relation between inflammation and neurodegeneration in multiple sclerosis brains. Brain. 2009;132(5):1175.

Kuhlmann T, Ludwin S, Prat A, Antel J, Brück W, Lassmann H. An updated histological classification system for multiple sclerosis lesions. Acta Neuropathol. 2017;133(1):13-24.

Absinta M, Sati P, Schindler M, et al. Persistent 7-tesla phase rim predicts poor outcome in new multiple sclerosis patient lesions. J Clin Invest. 2016;126(7):2597-2609.

Dal-Bianco A, Grabner G, Kronnerwetter C, et al. Slow expansion of multiple sclerosis iron rim lesions: pathology and 7 T magnetic resonance imaging. Acta Neuropathol. 2017;133(1):25-42.

Maggi P. Kuhle J, Schädelin S, et al. Chronic White Matter Inflammation and Serum Neurofilament Levels in Multiple Sclerosis. Neurology. 2021;97(6):e543-e553.

Absinta M, Maric D, Gharagozloo M, et al. A lymphocyte-microglia-astrocyte axis in chronic active multiple sclerosis. Nat 2021 5977878. 2021;597(7878):709-714.

Lucchinettil CF, Bruckz W, Lassmann H. Distinct Patterns of Multiple Sclerosis Pathology Indicates Heterogeneity in Pathogenesis. 1996;274:259-274.

Eshaghi A, Young AL, Wijeratne PA, et al. Identifying multiple sclerosis subtypes using unsupervised machine learning and MRI data. Nat Commun 2021 121. 2021;12(1):1-12.

Thompson AJ, Banwell BL, Barkhof F, et al. Diagnosis of multiple sclerosis: 2017 revisions of the McDonald criteria. Lancet Neurol. 2018;17(2):162-173.

Oh J, Suthiphosuwan S, Sati P, et al. Cognitive impairment, the central vein sign, and paramagnetic rim lesions in RIS. Mult Scler. 2021;27(14):2199-2208.

Tewarie P, Balk L, Costello F, et al. The OSCAR-IB consensus criteria for retinal OCT quality assessment. PLoS One. 2012;7(4):e34823.

Petzold A, Albrecht P, Balcer L, et al. Artificial intelligence extension of the OSCAR-IB criteria. Ann Clin Transl Neurol. 2021;8(7):1528-1542.

Lang A, Carass A, Hauser M, et al. Retinal layer segmentation of macular OCT images using boundary classification. Biomed Opt Express. 2013;4(7):1133-1152.

Lang A, Carass A, Al-Louzi O, et al. Combined registration and motion correction of longitudinal retinal OCT data. In: Progress in Biomedical Optics and Imaging—Proceedings of SPIE. vol. 9784. ; 2016.

Button J, Al-Louzi O, Lang A, et al. Disease-modifying therapies modulate retinal atrophy in multiple sclerosis: A retrospective study. Neurology. 2017;88(6):525-532.

Roy S, Butman JA, Reich DS, Calabresi PA, Pham DL. Multiple Sclerosis Lesion Segmentation from Brain MRI via Fully Convolutional Neural Networks. Published online Mar. 24, 2018. Accessed Mar. 16, 2020.

Van der Feen FE, de Haan GA, van der Lijn I, et al. Recognizing visual complaints in people with multiple sclerosis: Prevalence, nature and associations with key characteristics of MS. Mult Scler Relat Disord. 87. 2022;57:103429.

Oh J, Sotirchos ES, Saidha S, et al. In vivo demonstration of homonymous hemimacular loss of retinal ganglion cells due to a thalamic lesion using optical coherence tomography. JAMA Neurol. 89. 2013;70(3):410-411.

Holladay JT. Proper method for calculating average visual acuity. J Refract Surg. 1997; 13(4):388-391.

Tiew S, Lim C, Sivagnanasithiyar T. Using an excel spreadsheet to convert Snellen visual acuity to LogMAR visual acuity. Eye 2020 3411. 2020;34(11):2148-2149.

Gardiner SK, Mansberger SL, Demirel S. Detection of Functional Change Using Cluster Trend Analysis in Glaucoma. Invest Ophthalmol Vis Sci. 2017;58(6):BIO180-BIO190.

Lublin FD, Häring DA, Ganjgahl H, et al. How patients with multiple sclerosis acquire disability Brain. Published online Feb. 1, 2022.

Portaccio E, Bellinvia A, Fonderico M, et al. Progression is independent of relapse activity in early multiple sclerosis: a real-life cohort study. Brain. Published online Mar. 24, 2022.

Mann RS, Constantinescu CS, Tench CR. Upper cervical spinal cord cross-sectional area in relapsing remitting multiple sclerosis: Application of a new technique for measuring cross-sectional area on magnetic resonance images. J Magn Reson Imaging. 2007;26(1):61-65.

Van Buuren S, Fredriks M. Worm plot: a simple diagnostic device for modelling growth reference curves. Stat Med. 2001;20(8):1259-1277.

Al-Louzi O, Letchuman V, Manukyan S, et al. Central Vein Sign Profile of Newly Developing Lesions in Multiple Sclerosis. Neurol—Neuroimmunol Neuroinflammation. 2022;9(2):e1120.

Koch-Henriksen N, Sørensen PS. The changing demographic pattern of multiple sclerosis epidemiology. Lancet Neurol. 2010;9(5):520-532.

Reich DS, Smith SA, Gordon-Lipkin EM, et al. Damage to the Optic Radiation in Multiple Sclerosis Is Associated With Retinal Injury and Visual Disability. Arch Neurol. 2009;66(8):998-1006.

Absinta M, Sati P, Masuzzo F, et al. Association of Chronic Active Multiple Sclerosis Lesions with Disability in Vivo. JAMA Neurol. 2019;76(12):1474-1483.

Balcer LJ. Clinical practice. Optic neuritis. N Engl J Med. Mar. 23, 2006;354(12):1273-80.

Trip SA, Schlottmann PG, Jones SJ, et al. Optic nerve atrophy and retinal nerve fibre layer thinning following optic neuritis: evidence that axonal loss is a substrate of MRI-detected atrophy. Neuroimage. 2006;31(1):286-293.

(56)          References Cited

OTHER PUBLICATIONS

Saidha S, Sotirchos ES, Oh J, et al. Relationships between retinal axonal and neuronal measures and global central nervous system pathology in multiple sclerosis. JAMA Neurol. 2013;70(1):34-43.

Al-Louzi O, Hauptman H, Saidha S. Biopsy-negative PET-positive giant-cell arteritis. Neurology. Published online Oct. 1, 2014.

Kaisey M, Solomon A, Guerrero B, et al. Preventing multiple sclerosis misdiagnosis using the "central vein sign": A real-world study. Mult Scler Relat Disord. 2021;48.

Pellegrini F, Copetti M, Sormani MP, et al. Predicting disability progression in multiple sclerosis: Insights from advanced statistical modeling. Mult Scler J. 2020;26(14):1828-1836.

Tallantyre EC, Brookes MJ, Dixon JE, Morgan PS, Evangelou N, Morris PG. Demonstrating the perivascular distribution of MS lesions in vivo with 7-Tesla MRI. Neurology. 2008;70(22):2076-2078.

Mowry EM, Loguidice MJ, Daniels AB, et al. Vision related quality of life in multiple sclerosis: Correlation with new measures of low and high contrast letter acuity. J Neurol Neurosurg Psychiatry. 2009;80(7):767-772.

Lublin FD, Reingold SC. Defining the clinical course of multiple sclerosis: Results of an international survey. Neurology. 1996;46(4):907-911.

Jindahra P. Petrie A, Plant GT. The time course of retrograde trans-synaptic degeneration following occipital lobe damage in humans. Brain. 2012;135(Pt 2):534-541.

Sugimoto K, Schötzau A, Bergamin O, Zulauf M. Optimizing distribution and number of test locations in perimetry. Graefes Arch Clin Exp Ophthalmol. 1998;236(2):103-108.

Rigby RA, Stasinopoulos DM, Lane PW. Generalized additive models for location, scale and shape. J R Stat Soc Ser C (Applied Stat. 2005;54(3):507-554.

Gabilondo I, Martínez-Lapiscina EH, Martínez-Heras E, et al. Trans-synaptic axonal degeneration in the visual pathway in multiple sclerosis. Ann Neurol. 2014;75(1):98-107.

Al-Louzi O, Saidha S. Pathophysiology of Optic Neuritis. In: Multiple Sclerosis: A Mechanistic View. Elsevier; 2016:281-309.

Filippi M, Bar-Or A, Piehl F, et al. Multiple sclerosis. Nat Rev Dis Prim 2018 41. 2018;4(1):1-27.

Popescu BFG, Lucchinetti CF. Pathology of demyelinating diseases. Annu Rev Pathol Mech Dis. 2012;7:185-217.

Grambsch PM, Therneau TM. Proportional hazards tests and diagnostics based on weighted residuals. Biometrika. 1994;81(3):515-526.

* cited by examiner 302A
302B
302C
302D
302E
302F
302G
302H

400

402b

Left retina thickness map

74 μm

69 μm rTSD index: +5.7

225

150

75

0μm

402a

Right retina thickness map

75 μm

72 μm

502b

Left retina thickness map

74 µm

81 µm rTSD index: -6.4

225

150

75

0µm

502a

Right retina thickness map

73 µm

81 µm

SYSTEMS AND METHODS FOR QUANTIFYING RETROGRADE TRANS-SYNAPTIC DEGENERATION

CROSS-REFERENCE TO RELATED APPLICATIONS

This application claims priority to and the benefit of U.S. Provisional Patent Application. No. 63/497,698, filed Apr. 21, 2023, which is hereby incorporated by reference herein in its entirety.

STATEMENT REGARDING FEDERALLY SPONSORED RESEARCH OR DEVELOPMENT

This invention was made with Government support under Grant No. HT9425-23-1-0571 awarded by the Department of Defense. The Government has certain rights in the invention.

TECHNICAL FIELD

The present disclosure relates generally to systems and methods for quantifying retrograde trans-synaptic degeneration (rTSD), and more particularly, to systems and methods for quantifying rTSD based on the thicknesses of various retinal cell layers.

BACKGROUND

Multiple sclerosis (MS) is a chronic, immune-mediated, demyelinating disorder of the central nervous system, and one of the most common causes of neurological disability in young adults with rising incidence and economic burden. Despite significant advances in the understanding MS patho-biology, there are considerable gaps in the ability to accurately predict or halt disability progression in MS, especially in the progressive forms of the disease where effective therapies are extremely limited and show benefit primarily in the early stages when there is concomitant active inflammation. Therefore, there is a need to develop accurate biomarkers of neurodegeneration and disability progression in MS for use as outcome measures in clinical trials of neuroprotective therapies. Neuroaxonal degeneration is one of the main drivers of permanent clinical disability in MS. The exact mechanisms contributing to widespread neurode-generation, however, remain elusive and may harbor the key to understanding relapse-independent disability progression experienced by patients with MS (pwMS). Transsynaptic degeneration plays an important role in propagating neuronal loss in many neurological disorders by setting off a chain of neuronal degeneration anterograde and retrograde to the neuroaxonal unit directly affected, which may play a role in exacerbating relapse-independent disability in pwMS over time. The visual pathway lends itself readily to the investigation of trans-synaptic degeneration given an intricate structure-function correlation. Recent advances in optical coherence tomography (OCT), a reproducible, noninvasive retinal imaging technique, have enabled precise quantification of retinal layer thickness and assessment of the pre-geniculate visual pathway. When coupled with magnetic resonance imaging (MRI) of the post-geniculate visual pathway, this allows the in vivo investigation of mechanisms driving neurodegeneration across visual pathway synapses. Prior investigations have demonstrated that retrograde trans-synaptic degeneration (rTSD) of the retina occurs in response to some, but—importantly—not all MS lesions in the posterior visual pathway. The specific characteristics of MS lesions that promote trans-synaptic neuronal loss, versus those that do not, are poorly understood. Thus, new systems and methods for quantifying rTSD are needed.

SUMMARY

According to some implementations of the present disclosure, a method for quantifying retrograde trans-synaptic degeneration (rTSD) in a patient comprises receiving optical coherence tomography (OCT) image data associated with a left retina and a right retina of the patient. The method further comprises analyzing the OCT image data to determine a thickness of one or more retinal layers of the left retina and one or more retinal layers of the right retina. The method further comprises, based at least in part on the determined thicknesses, determining a value of an rTSD index that is indicative of a level of rTSD in the patient.

In some implementations, the rTSD index is based on the thicknesses of various layers of the patient's retina that are connected to the left optic radiation and the right optic radiation of the patient. In some implementations, the sign of the rTSD index indicates whether the cause of the rTSD (e.g., a paramagnetic rim lesion, a central vein sign lesion, or another lesion) is located in the left hemisphere of the patient's brain (e.g., the left optic radiation) or the right hemisphere of the patient's brain (e.g., the right optic radiation). In some implementations, the absolute value of the rTSD index indicates the magnitude of the rTSD in one hemisphere of the patient's brain relative to the other hemisphere of the patient's brain.

The above summary is not intended to represent each implementation or every aspect of the present disclosure. Additional features and benefits of the present disclosure are apparent from the detailed description and figures set forth below.

BRIEF DESCRIPTION OF THE DRAWINGS

The disclosure, and its advantages and drawings, will be better understood from the following description of representative embodiments together with reference to the accompanying drawings. These drawings depict only representative embodiments, and are therefore not to be considered as limitations on the scope of the various embodiments or claims.

Figures 1, 2:
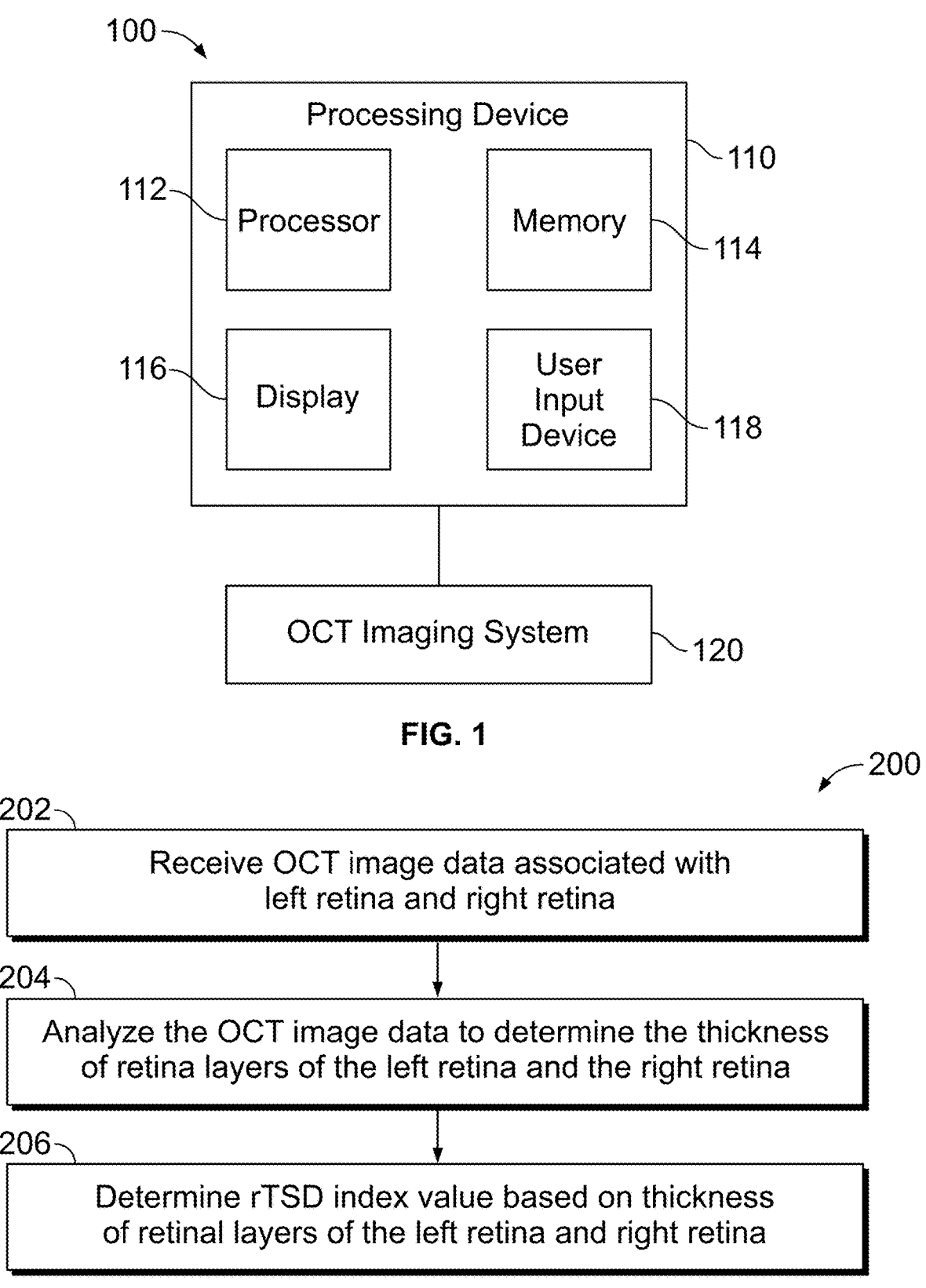
FIG. 1 shows a system for implementing a method for quantifying retrograde trans-synaptic degeneration (rTSD) in a patient, according to aspects of the present disclosure.
FIG. 2 shows a flowchart of a method for quantifying retrograde trans-synaptic degeneration (rTSD) in a patient, according to aspects of the present disclosure.

While the invention is susceptible to various modifications and alternative forms, specific implementations have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

FIG. 1 is a block diagram of an example system 100 for implementing any of the herein-discussed features, methods, processes, etc. For example, system 100 can be used to perform a method for quantifying retrograde trans-synaptic degeneration (rTSD) in a patient using optical coherence tomography (OCT) image data. The system 100 can include one or more processing devices 100, which can each include any one or more of a processor 112, a memory 114, a display 116, a user input device 118, and/or other components. The memory 114 can include machine-readable instructions for executing one or more machine learning models. The processor 112 can execute these instructions to implement the one or more machine learning models. The memory 114 can also store the OCT image data.

The processing device 110 can include any suitable processing device, such as general purpose computer systems, microprocessors, digital signal processors, micro-controllers, application specific integrated circuits (ASICs), programmable logic devices (PLDs), field programmable logic devices (FPLDs), programmable gate arrays (PGAs), field programmable gate arrays (FPGAs), mobile devices such as mobile telephones, personal digital assistants (PDAs), or tablet computers, local servers, remote servers, wearable computers, or the like. The memory device 114 can include any suitable memory device and/or machine-readable medium that is capable of storing, encoding, and/or carrying a set of instructions for execution by a processing device and that cause the processing device to perform and/or implement any of the features discussed herein, including solid-state memories, optical media, magnetic media, random access memory (RAM), read only memory (ROM), a floppy disk, a hard disk, a CD ROM, a DVD ROM, flash memory, or other computer readable medium that is read from and/or written to by a magnetic, optical, or other reading and/or writing system that is coupled to the processing device, can be used for the memory or memories.

The display 116 can be used to display any information associated with the features disclosed herein, including information associated with the level of rTSD in the patient.

The display device 116 can be any known display technology, including but not limited to display devices using Liquid Crystal Display (LCD) or Light Emitting Diode (LED) technology. The user input device 118 can be used to allow the user to interact with the system 100 for any suitable purpose, including initiating, pausing, or terminating the analysis of the OCT image data. In some implementations, the system 100 includes an OCT imaging system 120 that generates the OCT image data. The OCT imaging system 120 can generally be any suitable type of OCT imaging system. In other implementations, the system 100 does not include the OCT imaging system, but instead receives OCT image data from an external source.

FIG. 2 shows a flowchart of a method 200 for quantifying retrograde trans-synaptic degeneration (rTSD) in a patient, according to aspects of the present disclosure. rTSD can have a variety of different causes, such as abnormalities in the left and/or right optic radiation of the patient. The optic radiation are the axons from the neurons in the lateral geniculate nucleus to the primary visual cortex. These abnormalities can include lesions in the optic radiations, such as a paramagnetic rim lesion, a central vein sign+ (CVS+) lesion, and others.

Figure 3:
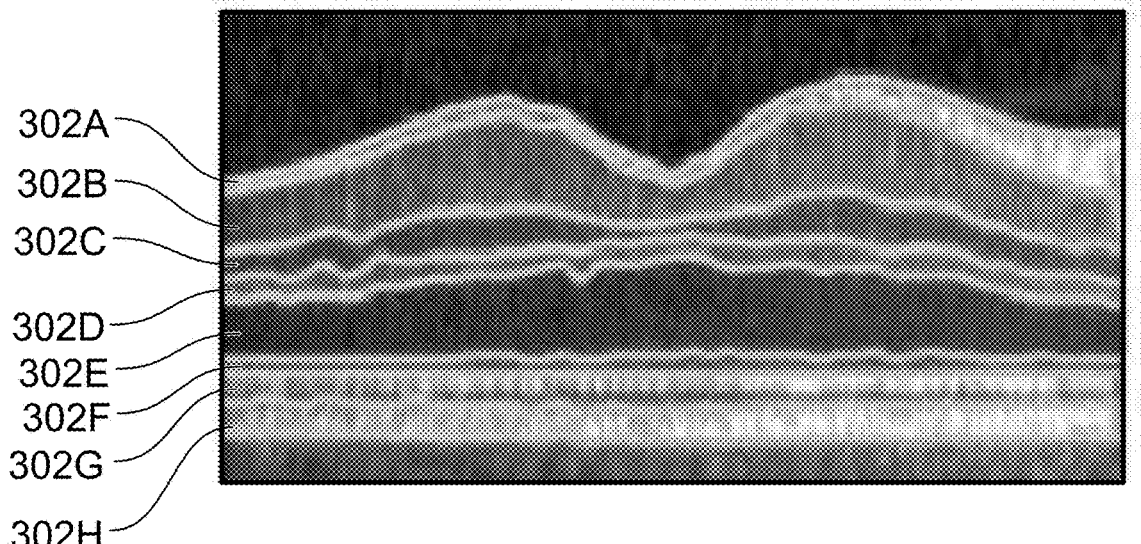
FIG. 3 is an image showing segmentation of retinal layers in an OCT image, according to aspects of the present disclosure.

Step 202 includes receiving optical coherence tomography (OCT) image data associated with the left retina and the right retina of the patient. Step 204 includes analyzing the OCT image data to determine the thickness of one or more retinal layers of the left retina and one or more retinal layers of the right retina. In some implementations, step 204 includes first segmenting the left retina and the right retina within the OCT image data to identify the retinal layers of the left retina and the right retina, and then determining the thicknesses of the needed layers. FIG. 3 illustrates an example segmentation of retinal layers. As shown, segmentation was used to identify retinal layers 302A-302GH. This process can be performed on the OCT image data for both retinas of the patient to identify the layers and determine the corresponding thicknesses.

In some implementations, the retinal layers of each retina can include the temporal ganglion cell and inner plexiform layer (temporal GCIPL), the nasal ganglion cell and inner plexiform layer (nasal GCIPL), the temporal inner nuclear layers (INL), the temporal outer nuclear layers (ONL), and others. In in some implementations, step 204 includes determining the thickness of the left temporal GCIPL, the left nasal GCIPL, the right temporal GCIPL, and the right nasal GCIPL.

The various retinal layers can be grouped according to which optic radiation of the patient they are connected to. Retinal layers on the left sides of the patient's eyes are connected to the left optic radiation, while retinal layers on the right side of the patient's eyes are connected to the right optic radiation. Thus, a first group of retinal layers includes the left temporal GCIPL and the right nasal GCIPL, which are on the left side of the left retina and the left side of the right retina, respectively, and are both connected to the left optic radiation. A second one group of retinal layers includes the right temporal GCIPL and the left nasal GCIPL, which are on the right side of the right retina and the right side of the left retina, respectively, and are both connected to the right optic radiation. The first group may also include the left temporal INL and the left temporal ONL. The second group may also include the right temporal INL and the right temporal ONL.

Step 206 of method 200 includes determining the value of an rTSD index based at least in part on the determined thicknesses. The rTSD index is a number that is indicative of the level of rTSD in the patient. In some cases, the value of the rTSD index relative to 0 is indicative of whether the cause of the rTSD in the patient (e.g., a lesion) is located in the left hemisphere of the patient (e.g., in the left optic radiation) or in the right hemisphere of the patient (e.g., in the right optic radiation). In some cases, the absolute value of the rTSD index is indicative of the magnitude of the rTSD in one hemisphere relative to the other.

In a first implementation, the rTSD index is based on the ratio of (i) the GCIPL projections to the left posterior visual pathway (e.g., the left optic radiation) to (ii) the GCIPL projections to the right posterior visual pathway (e.g., the right optic radiation). In these implementations, the GCIPL projections to the left posterior visual pathway include the combined thickness of the retinal layers that are located on the left side of the left and right retinas (e.g., the retinal layers connected to the left optic radiation. The GCIPL projections to the right posterior visual pathway include the combined thickness of the retinal layers that are located on the right side of the left and right retinas (e.g., the retinal layers connected to the right optic radiation).

In the first implementation, the rTSD index can be calculated according to equation (1):

$$rTSD_{index} =$$

$$\left(\frac{\text{left temporal } GCIPL \text{ thickness} + \text{right nasal } GCIPL \text{ thickness}}{\text{right temporal } GCIPL \text{ thickness} + \text{left nasal } GCIP \text{ thickness}} - 1\right) \times 100.$$

In this equation, the value of the rTSD index being greater than 0 indicates that the cause of the rTSD index is located in the left hemisphere of the brain, and the value of the rTSD index being less than 0 indicates that the cause of the rTSD index is located in the right hemisphere of the brain.

In a second implementation, the rTSD index is based on the average of (a) the ratio of (i) retinal projections to the left posterior visual pathway from the left retina (e.g., the thickness of the left temporal GCIPL, which is connected to the left optic radiation) and (ii) retinal projections to the right posterior visual pathway from the left retina (e.g., the thickness of the left nasal GCIPL, which is connected to the right optic radiation), and (b) the ratio of (i) retinal projections to the left posterior visual pathway from the right retina (e.g., the thickness of the right nasal GCIPL, which is connected to the left optic radiation) and (ii) retinal projections to the right posterior visual pathway from the right retina (e.g., the thickness of the right temporal GCIPL, which is connected to the right optic radiation).

In the second implementation, the rTSD index can be calculated according to equation (2):

$$rTSD_{index} =$$

$$\left(\left(\left(\frac{\text{right nasal } GCIPL \text{ thickness}}{\text{right temporal } GCIPL \text{ thickness}} + \frac{\text{left temporal } GCIPL \text{ thickness}}{\text{left nasal } GCIPL \text{ thickness}}\right) \times \frac{1}{2}\right) - 1\right) \times 100.$$

Again in this equation, the value of the rTSD index being greater than 0 indicates that the cause of the rTSD index is located in the left hemisphere of the brain, and the value of the rTSD index being less than 0 indicates that the cause of the rTSD index is located in the right hemisphere of the brain.

In general, either equation (1) or equation (2) can be used to determine the value of the rTSD index in step 206 of method 200.

Figure 4A:
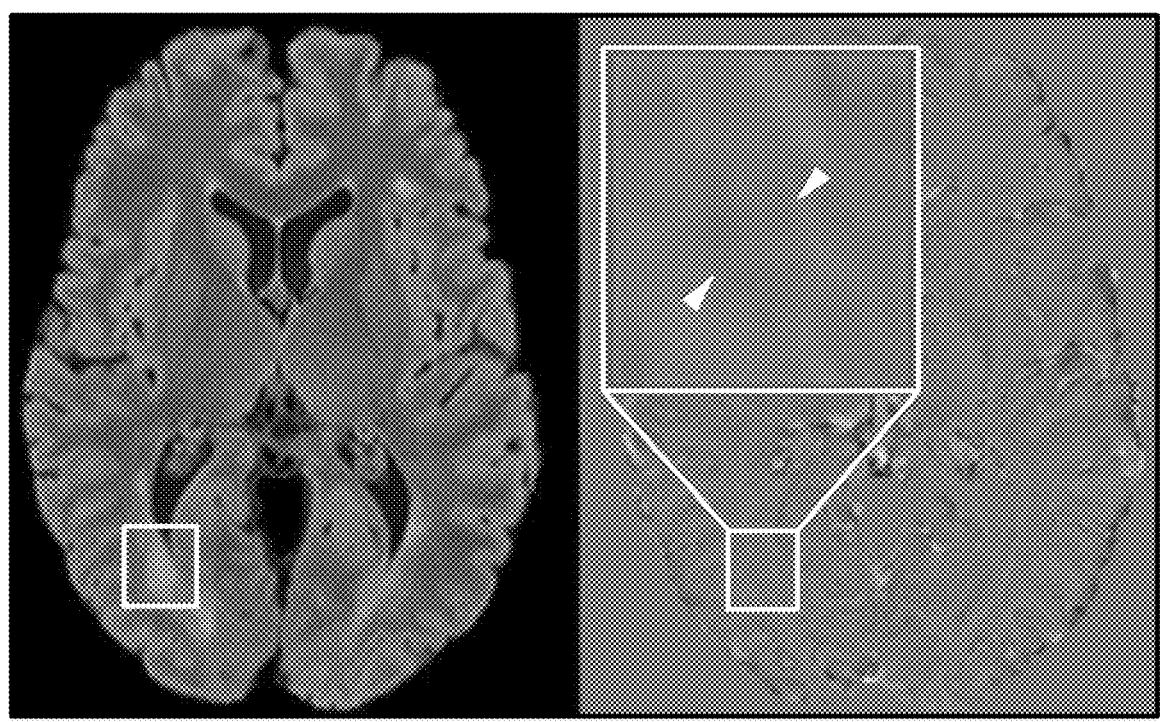
FIG. 4A is an MRI image showing a right optic radiation paramagnetic lesion in the brain of a patient, according to aspects of the present disclosure.
Figures 4B, 4C:
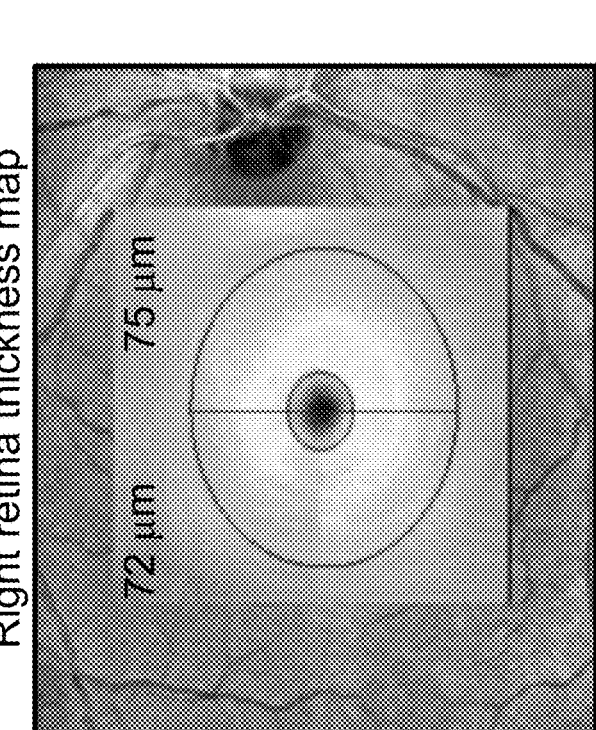
FIG. 4B is a thickness map of the layers of the right retina of the patient of FIG. 4A, according to aspects of the present disclosure.
FIG. 4C is a thickness map of the layers of the left retina of the patient of FIG. 4A, according to aspects of the present disclosure.

FIGS. 4A-4C demonstrate the use of method 200 in a patient having a right optic radiation paramagnetic lesion. FIG. 4A is a T2*-weighted MRI image 400 of the patient's brain from the underside, showing the lesion in the right hemisphere. FIG. 4B is retina thickness map 402A of the right retina and FIG. 4C is a retina thickness map 402B of the left retina, from the perspective of facing toward the patient. Thickness maps 402A and 402B demonstrate the thinning of the retina layers on the right side of the right retina, and the right side of the right retina, corresponding to the right optic radiation paramagnetic lesion.

Figure 5A:
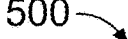
FIG. 5A is an MRI image showing a left optic radiation paramagnetic lesion in the brain of a patient, according to aspects of the present disclosure.
Figure 5A:
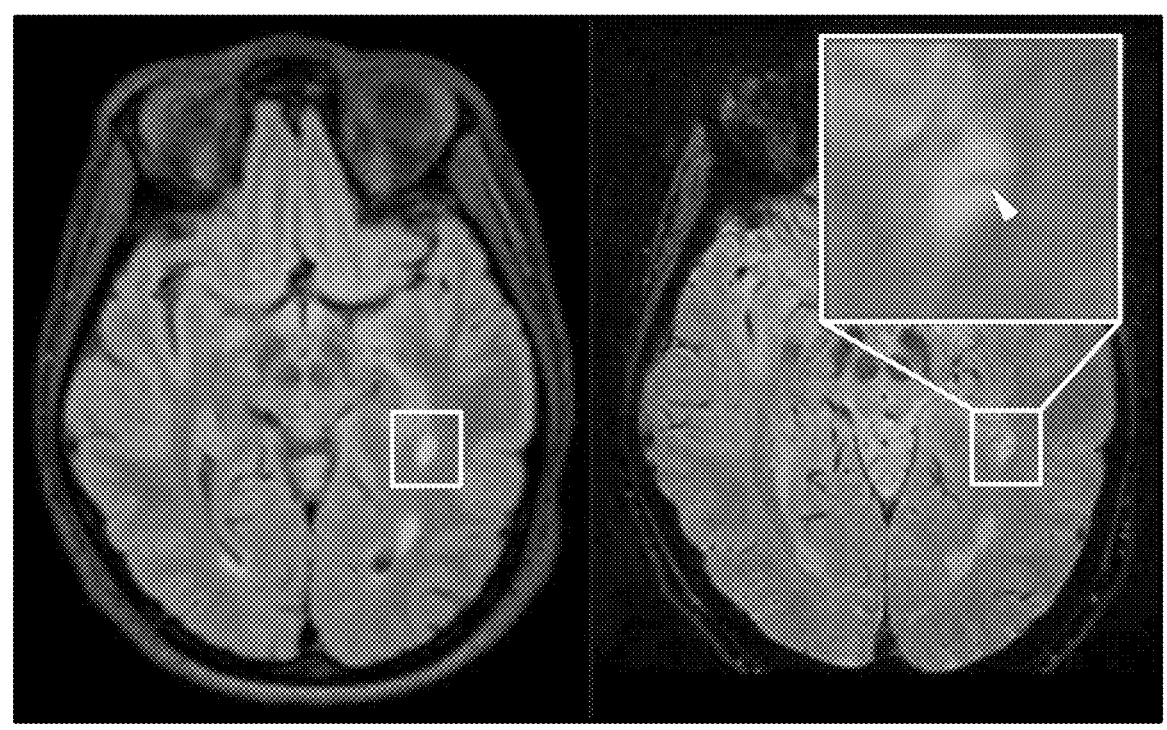
Figures 5B, 5C:
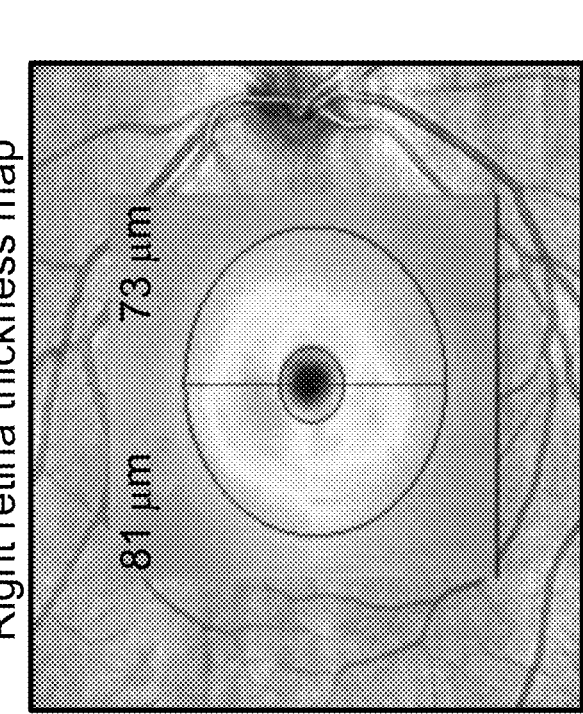
FIG. 5B is a thickness map of the layers of the right retina of the patient of FIG. 5A, according to aspects of the present disclosure.
FIG. 5C is a thickness map of the layers of the left retina of the patient of FIG. 5A, according to aspects of the present disclosure.

FIGS. 5A-5C demonstrate the use of method 200 in a patient having a left optic radiation paramagnetic lesion. FIG. 5A is a T2*-weighted MRI image 500 of the patient's brain from the underside, showing the lesion in the left hemisphere. FIG. 5B is retina thickness map 502A of the right retina and FIG. 5C is a retina thickness map 502B of the left retina, from the perspective of facing toward the patient. Thickness maps 502A and 502B demonstrate the thinning of the retina layers on the left side of the right retina, and the left side of the right retina, corresponding to the left optic radiation paramagnetic lesion.

Figure 6:
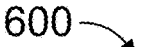
FIG. 6 is a plot of the distribution of rTSD index values for MS patients and non-MS patients, according to aspects of the present disclosure.
Figure 7:
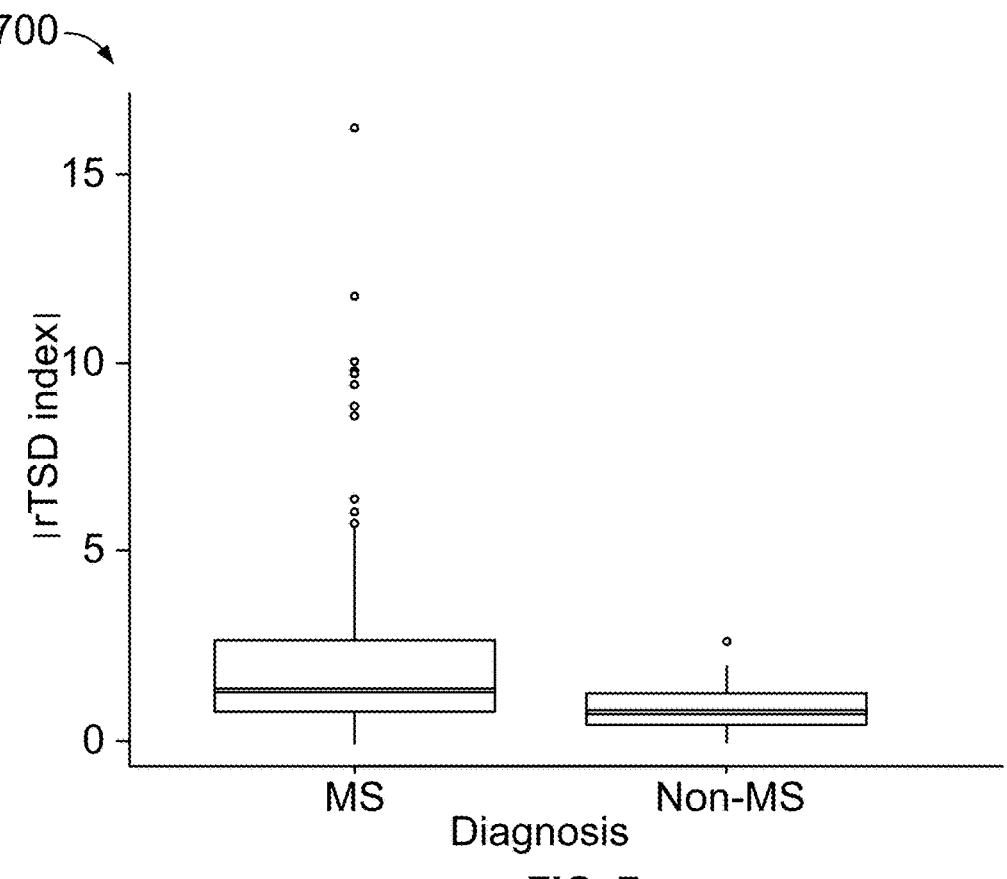
FIG. 7 is a plot of the distribution of the absolute value of rTSD index values for MS patients and non-MS patients, according to aspects of the present disclosure.

In some cases, the absolute value of the rTSD index in some cases is indicative of the patient having multiple sclerosis (MS). FIG. 6 is plot 600A of the calculated rTSD index for MS patients, and plot 600B of the calculated rTSD index for non-MS patients. As shown, the rTSD index values for non-MS patient generally do not fall outside of a range from about −3 to 3, while the rTSD index value for some MS patients do fall outside of that range. Similarly, FIG. 7 is a plot 700 of the magnitude of the rTSD index values for MS patients and non-MS patients. As shown, the magnitudes of the rTSD index value for the MS patients ranges much larger than for non-MS patients. Thus, in some cases, the value of the rTSD index being greater than or equal to 3, less than or equal to −3, or both, is an indication that the patient has MS.

Figure 8:
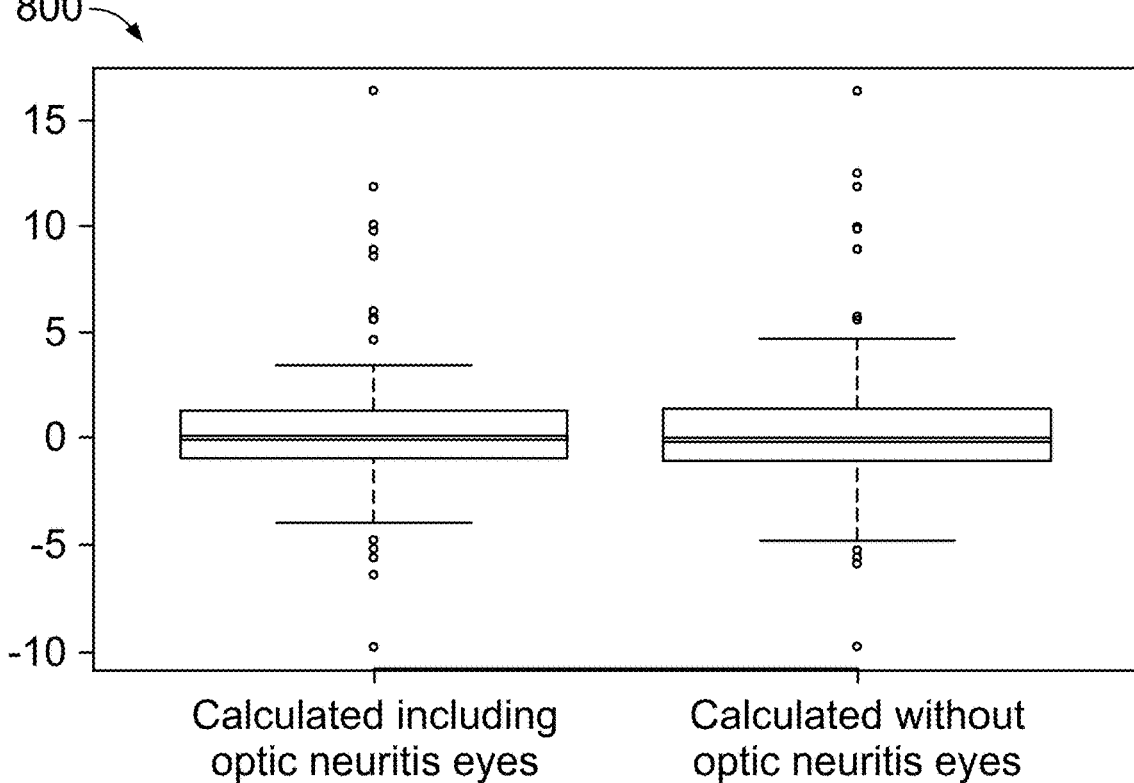
FIG. 8 is a plot of the distribution of rTSD index values for a sample of eyes and for the sample of eyes excluding eyes having optic neuritis, according to aspects of the present disclosure.

Referring now to FIG. 8, the determination of the rTSD index is robust to the presence of optic neuritis (ON). FIG. 8 is a plot 800 showing rTSD index values for a sample that includes eyes diagnosed with ON (left), and for the same sample but excluding the eyes diagnoses with ON (right). As shown, eyes with ON generally have no statistically significant effect on the rTSD index values.

In some implementations, the absolute value of the rTSD index is indicative of the severity of hemimacular ganglion cell atrophy in at least one hemisphere of the patient's brain, the level of dysfunction in the visual field of the patient, or both.

Disclosed below is an example study associated with method 200.

Several advanced MRI biomarkers have been validated in the stratification of MS lesions and in vivo detection of clinically relevant pathologies, such as the central vein sign (CVS), a biomarker of perivenular inflammation, and paramagnetic rim lesions (PRLs), a biomarker of chronic active inflammation in MS lesions. The overall goal of this project is to leverage advanced OCT-MRI analysis to understand how specific lesion types, reflecting distinct pathologies in MS, contribute to rTSD in a cohort of 80 pwMS followed longitudinally over 4 years. This project will pursue the following specific aims.

Specific Aim 1 includes Determining whether CVS+/PRL burden in the post-geniculate visual pathway drives a greater extent of rTSD on OCT. Aim 1 hypothesis: A higher burden of CVS+ and/or PRLs will be associated with a greater extent of rTSD on OCT at baseline (compared to conventional lesion burden measures), and a higher rate of retinal neurodegeneration longitudinally over a 4-year period.

Specific Aim 2 includes investigating the impact of rTSD, CVS+ and/or PRLs in the post-geniculate visual pathway on visual function. High/low contrast visual acuity and standard automated perimetry will be obtained annually to track progressive hemifield visual defects. Aim 2 hypothesis: CVS+ and/or PRLs in the post-geniculate visual pathway will exhibit worse contralateral hemifield visual defects on perimetry at baseline (compared to CVS−/PRL− lesions and/or normal rTSD index), and higher risk of visual field defect progression over follow-up.

Specific Aim 3 includes assessing whether rTSD of the visual pathway is linked to accelerated brain and cervical spinal cord neurodegeneration, and disability progression independent of relapse activity (PIRA). Aim 3 hypothesis: PwMS with evidence of rTSD of the visual pathway will exhibit accelerated brain and spinal cord degeneration, and higher risk of PIRA over a 4-year follow-up period adjusting for clinical characteristics, disease modifying therapy, and lesion load measures.

By developing methods to effectively combine information from OCT and MRI, this study will provide unique insights into the association between hemimacular rTSD and specific lesion subtypes in the visual pathway of pwMS, as well as its functional and clinical impact. If successful, these findings will lay the groundwork for potential application of easily acquired rTSD measures in future clinical trials of neuroprotective therapies in progressive MS and, by extension, other neurodegenerative disorders.

Research Strategy

1. Significance 1.1 MS-Related Visual Impairment and Disability Cause Significant Morbidity in Clinical Practice Multiple sclerosis (MS) is a chronic incurable disorder characterized by inflammatory demyelination within the brain, visual pathway, and spinal cord, and is one of the most common causes of neurological disability in young adults. The economic burden of MS in the United States is significant with recent total estimates of $85.4 billion, and lifetime costs for individual patients exceeding $4 million. Visual dysfunction is common in MS and has been linked to inflammatory demyelinating lesions in the visual pathway. It is estimated that 70% of people with MS (pwMS) experience visual symptoms at some point during the course of illness, with visual disability having an important impact on patient-reported quality of life reduction.

Relapsing-remitting MS (RRMS) is the most common form of MS, accounting for 80-85% of cases and characterized by discrete clinical symptoms caused by acute inflammatory lesions. Approximately 30-40% of RRMS patients are at risk of transitioning to a disease course dominated by slow and unrelenting disability progression in the absence of active inflammation, known as secondary progressive MS (SPMS). This transition occurs at a median of 6-15 years from RRMS onset, and is more likely with high early relapse frequency, suggesting that early inflammatory demyelinating lesions can result in long-term effects promoting disability progression over subsequent decades. A smaller proportion of pwMS have primary progressive MS (PPMS), which is characterized by progressive disability accumulation in the absence of discrete relapses, despite exhibiting remarkably similar demyelinating lesions on magnetic resonance imaging (MRI). In all forms of the disease, neurodegeneration starts early, may accelerate over time, and contributes to irreversible clinical disability. The exact mechanisms promoting neurodegeneration in the absence of inflammation in susceptible individuals and its association with long-term visual, cognitive, and/or physical disability progression remain poorly understood and difficult to predict in clinical practice. The majority of currently approved MS therapies are aimed at suppressing breakthrough inflammation, but no treatments are available to slow or reverse ongoing neurodegeneration, which invariably occurs throughout the disease course.

1.2 Trans-Synaptic Degeneration Amplifies Neuronal Loss in MS and Other Neurological Disorders.

One mechanism contributing to the widespread neurodegeneration in MS is trans-synaptic degeneration (TSD). TSD refers to the phenomenon whereby injury in one neuroaxonal unit propagates through synapses, resulting in a chain effect of upstream and/or downstream neuronal loss. TSD has been reported in various neurological disorders, such as Alzheimer's disease, Parkinson's disease, amyotrophic lateral sclerosis, and ischemic stroke, suggesting shared mechanisms and vulnerability to trans-synaptic neuronal loss.

Understanding the mechanisms promoting trans-synaptic neuronal loss maybe key in explaining disability progression independent of relapses or new inflammatory activity in MS, thereby opening windows for novel therapeutic interventions to halt the spread of neurodegeneration at the cellular level. The visual pathway is well-suited to the in vivo study of TSD in MS and other neurological disorders. OCT is a reproducible, noninvasive imaging technique that uses near-infrared light to generate high-resolution retinal images. Specialized OCT segmentation algorithms allow the measurement of discrete retinal layer thickness, thereby enabling precise assessment of the pre-geniculate visual pathway. The human retina is unmyelinated, thereby providing a major advantage of using OCT to track neurodegeneration in MS given the absence of confounding effects from demyelination. The PI and other groups have shown that atrophy of the peripapillary retinal nerve fiber layer (pRNFL), and ganglion cell and inner plexiform layers (GCIPL) reflect global measures of whole brain and gray matter atrophy, serving as an accurate measure of neuronal loss in MS, and are associated with visual and clinical disability. Recent work has further highlighted the utility of GCIPL thickness for predicting long-term MS-related disability, suggesting that retinal neurodegeneration reflects global mechanisms of MS disease progression, but the exact mechanistic link remains to be identified.

Retrograde trans-synaptic degeneration (rTSD) has been demonstrated in the visual pathway of pwMS through direct in vivo analysis of retinal ganglion cells and their axonal projections in relation to posterior visual pathway lesions. The PI has previously demonstrated that rTSD in the visual pathway results in GCIPL thinning in corresponding ipsilateral temporal and contralateral nasal hemimacular regions of pwMS. Importantly, rTSD does not uniformly occur with all MS lesions in the posterior visual pathway, which presents a unique opportunity to investigate lesional and/or subject-specific factors promoting this phenomenon. Furthermore, most studies of rTSD were either qualitative or incorporate average thicknesses per eye (which confounds rTSD localization due to inclusion of bihemispheric projections). Therefore, developing novel methods to precisely quantify rTSD has potential value in the detection of neurodegenerative sequelae from focal MS lesions.

1.3 the Central Vein Sign (CVS): Characterizing Perivenular Inflammation in MS Using Advanced MRI.

Conventional T2 lesion measures in pwMS show modest correlation with long-term disability and reflect a broad spectrum of pathological processes (demyelination, edema, gliosis, ischemia/infarction), which are not specific to MS and can occur due to other neurological conditions, such as cerebral small vessel disease or migraine. The central vein sign (CVS) is a linear hypointensity within lesions, visualized on susceptibility-based MRI corresponding to a small vein/venule. The CVS allows the in vivo assessment of perivenular inflammation, which is characteristic of MS lesions, and the percentage of lesions with the CVS on optimized T2*-weighted imaging has been previously shown to effectively differentiate MS from other mimicking conditions.

We have recently demonstrated that the majority of new lesions in pwMS were CVS+, as opposed to those which formed in other mimicking conditions. These findings highlight that the CVS is not only useful for the diagnosis of MS but also for the radiological characterization of new lesions to differentiate MS-related from non-specific T2 lesions over time. However, whether the extent of perivenular inflammation in the posterior visual pathway, as reflected by the CVS lesion count or percentage (a more specific measure of MS lesion burden), drives a greater extent of rTSD on OCT is still unknown.

1.4 Paramagnetic Rim Lesions (PRLs): A Window into Chronic Active Inflammation in MS There is stark variability in the extent of persistent chronic active inflammation, remyelination, axonal transection, and overall repair within MS lesions following the acute inflammatory demyelinating phase. In a subset of lesions, chronic inflammation persists in the form of iron-rich mononuclear infiltrate, mainly consisting of activated microphages and/or microglia, concentrated at the lesion edge. These chronic active MS lesions also exhibit various extents of active myelin breakdown and axonal loss consistent with ongoing tissue injury. The iron-rich cellular content at the chronic active lesion edge can be detected in vivo as a paramagnetic signal on susceptibility-based MRI techniques, hence the term paramagnetic rim lesions (PRLs). PRLs have been shown to be associated with elevated serum neurofilament light chain (sNfL) levels, suggestive of ongoing neuroaxonal damage, and accelerated clinical disability progression. Transcriptional profiling of these lesions at the single-nucleus RNA sequencing level has demonstrated the role of complement component 1q (C1q) as a prominent mediator of microglia-driven chronic neuroinflammation. It is unclear whether persistent chronic inflammation in MS, however, drives a greater extent of trans-synaptic neuronal loss, thereby explaining the accelerated rates of clinical disability observed in this subgroup of patients.

In this proposal, it is hypothesized that perivenular inflammation (as reflected by the CVS) and/or chronic active inflammation (as reflected by PRLs) in the posterior visual pathway are more likely to cause rTSD in the retina of pwMS, worse visual dysfunction over time, and that these differences can be detected using neuroanatomically consistent OCT and perimetry analysis of the hemimacular retinal ganglion cell projections.

2. Innovation 2.1 Quantifying Neuroanatomically Consistent rTSD in the Human Visual Pathway.

One of the main innovative ideas to be tackled in this project is developing novel methodology to measure rTSD in hemimacular retinal ganglion cell projections. Building upon previous findings showing that hemimacular retinal ganglion cell loss occurs due to posterior visual pathway lesions, a specialized OCT analysis workflow has been designed to quantify GCIPL thickness within nasal and temporal regions within each eye corresponding to posterior visual pathway projections. These measures will be used to compute monocular and binocular rTSD indices, measured as the ratio between nasal and temporal macular GCIPL thickness for each eye individually (which enables computation of this measure if one eye is excluded due to history of optic neuritis), or—alternatively—a ratio of temporal ipsilateral and nasal contralateral GCIPL measures in both eyes reflecting the extent of rTSD driven by one hemisphere relative to the other (i.e. rTSD index). This novel approach will precisely isolate the effects of posterior visual pathway lesions by measuring hemisphere-driven rTSD within specific corresponding retinal compartments.

2.2 Association of Distinct MS Lesion Profiles on Advanced Susceptibility-Based MRI with rTSD MS lesions exhibit variable extents of chronic persistent inflammation, remyelination, axonal transection and irreversible tissue injury on histopathological analysis. Interestingly, studies have shown that pwMS with lesion-led subtypes (reflecting ongoing accumulation of lesions on imaging) had the highest risk of confirmed disability progression. However, the understanding of which lesion type (s) driving this progression and their underlying pathobiological mechanisms remains limited. This project will introduce novel methodology to study the relationship between distinct MS lesion profiles on susceptibility-based MRI, reflecting pathologically specific disease mechanisms, with the presence and severity of rTSD in the anterior visual pathway projections using customized OCT analysis and retinal layer segmentation.

2.3 Exploring the Relationship Between rTSD, Disability Accumulation, and Global Neurodegeneration in MS.

The occurrence of rTSD due to focal inflammatory lesions results in amplification of the neuronal injury through a chain of degenerative effects. However, it is unclear if patients who are more susceptible to rTSD of the visual pathway are at higher risk of TSD from lesions in other parts of the central nervous system resulting in faster rates of global neurodegeneration. This proposal will explore whether rTSD of the visual pathway can act as a surrogate for individual patient susceptibility to TSD, accelerated whole brain and spinal cord degeneration, and is predictive of a higher risk of disability progression. These results will pave the way for assessing the potential use of easily acquired rTSD measures in the visual pathway for use as outcome measures in future clinical trials of neuroprotective therapies.

3. Approach 3.1 Recruitment and Study Design (Aims 1, 2, and 3).

Aim 1: Determine whether CVS+/PRL burden in the post-geniculate visual pathway drives a greater extent of rTSD on OCT.

Rationale and preliminary data: One of the main challenges in MS clinical practice is the heterogeneity of underlying lesions, pathobiological mechanisms driving neuronal loss, and—consequently—risks of disability accumulation. Therefore, identifying lesion subtypes that have a higher risk of triggering downstream or upstream neurodegenerative effects is critical for disability prognostication and enrichment of clinical trials of targeted neuroprotective therapies. CVS and PRLs in MS reflect unique underlying mechanisms of tissue injury (perivenular and chronic active inflammation respectively), which show high specificity for MS lesions.

Higher CVS lesion burden has been linked to cognitive impairment, particularly verbal memory, while PRLs are associated with slow lesion expansion, faster rates of brain atrophy, and accelerated motor and cognitive disability progression. However, whether these effects are mediated by rTSD is unknown and, in this proposal, this question will be answered by using the visual pathway as a model of this process.

The CVS is specific for perivenular inflammation and is present in the majority of newly forming MS lesions. In a pilot study conducted at the NINDS/NIH, MRI histopathology correlation of the CVS from 5 MS and 1 control autopsy cases was analyzed. A total of 26 lesions (19 CVS+ and 7 CVS−) were examined using the combination of post-mortem MRI and histopathological characterization of the CVS. Of the 24 lesions assessed in the MS cases, 21/24 (87.5%) were chronic inactive and 3/24 (12.5%) were chronic active. The CVS showed excellent specificity for the detection of central vein/venules on neuropathological analysis in both types (0/7 false positives), confirming its utility for the in vivo detection of perivenular inflammation in pwMS using the same MRI sequence employed in this proposal.

We further characterized the CVS in a cohort of 141 pwMS (80 RRMS, 28 SPMS, 33 PPMS) followed longitudinally over a median duration of 2.7±3 years. The CVS was present in the majority of newly developing T2/enhancing lesions (159/233; 68%) and was associated with increased rates of disease modifying therapy escalation due to worsening disease activity. Interestingly, CVS+ lesion count was associated with a lower brain parenchymal fraction (β: −0.04% per each additional CVS+ lesion; 95% CI: −0.02, −0.06), adjusting for age, sex, disease subtype and baseline disease modifying therapy, suggesting accelerated neurodegeneration in cases with higher CVS+ lesion burden. This relationship was not significant for CVS percentage indicating that higher cumulative lesion numbers have a greater weight than the proportion of CVS+ lesions, particularly in cases with an overall low total number of lesions but high CVS percentage.

Hypothesis: A higher burden of CVS+ and/or PRLs in the post-geniculate visual pathway will be associated with a greater extent of rTSD of the homonymous hemimacular GCIPL projections at baseline, and higher rates of GCIPL thinning longitudinally.

Experimental Design: Spectral-domain OCT scans will be performed annually on study participants using a Cirrus HD-OCT device (model 5000, software version 11.5.2; Carl Zeiss Meditec, Dublin, CA). Scans with signal strength less than 7/10 or with motion artifacts will be excluded. All scans will be reviewed to ensure adequate quality according to the OSCAR-IB criteria.79,80 Macular OCT segmentation will be performed using an automated system to compute thicknesses of the GCIPL, inner nuclear layer (INL), outer nuclear layer (ONL), and average macular thickness (AMT) as described in detail in previous projects led by the PI. Specific retinal layer thickness measures will be captured in four macular quadrants per eye: nasal superior, nasal inferior, temporal superior, and temporal inferior. These measures will be combined to calculate a "rTSD index", a novel measure to quantify the extent of rTSD of the visual pathway, calculated as:

$$rTSD_{index} = \left( \frac{\text{left temporal thickness} + \text{right nasal } GCIPL \text{ thickness}}{\text{right temporal thickness} + \text{left nasal } GCIP \text{ thickness}} - 1 \right) \times 100, \text{ and/or}$$

$$rTSD_{index} = \left( \left( \left( \frac{\text{right nasal } GCIPL \text{ thickness}}{\text{right temporal } GCIPL \text{ thickness}} + \frac{\text{left temporal } GCIPL \text{ thickness}}{\text{left nasal } GCIPL \text{ thickness}} \right) \times \frac{1}{2} \right) - 1 \right) \times 100,$$

where positive rTSD index values indicate right hemisphere driven loss of GCIPL thickness (i.e., lower denominator driving the value of the ratio to be greater than 1), while negative numbers indicate similar GCIPL loss driven by the left hemisphere (lower numerator driving the value of the ratio to be less than 1). Absolute values of the rTSD index reflect the magnitude of rTSDdriven GCIPL loss by the affected hemisphere relative to the contralateral side. This has the advantage of normalizing GCIPL thickness values to the contralateral side across subjects and controlling for monocular effects of optic neuritis, where GCIPL loss is relatively symmetric across the nasal/temporal hemimacula within affected eyes. In a preliminary analysis of 55 MS patients with OCT image data, an rTSD cut-off of ≥4 or ≤−4 showed a positive predictive value of 93% in the detection of rTSD driven by hemisphere-specific postgeniculate lesions confirmed on MRI (overall prevalence 14/55; 25%). The novel methodology of combining hemimacular thickness measures in one index will enable the generation of a quick and easy to interpret read-out from OCT image data that indicates the direction (i.e., right vs left hemisphere) and magnitude (i.e., absolute index value) of rTSD on OCT scans.

Research MRI scans will be performed annually on a Skyra 3 tesla (3T) scanner (Siemens Healthineers, Erlangen, Germany). The study protocol will include whole brain 3D T1 weighted magnetization-prepared rapid acquisition of gradient echoes (T1 MPRAGE), 3D T2-weighted fluid-attenuated inversion recovery (FLAIR), echo-planar diffusion tensor imaging (DTI), and optimized T2*-weighted, whole brain, three-dimensional (3D)-segmented echo-planar imaging, which will be used for the simultaneous assessment of CVS and PRLs in the post-geniculate visual pathway. MS lesion segmentation will be performed using a deep learning method designed and implemented by the PI in several previous projects. DTI tractography and optic radiation segmentation will be performed using a validated algorithm. Lesion masks will be overlaid on optic radiation segmentation for accurate co-localization of lesions in the post-geniculate visual pathway. CVS and/or PRLs will be evaluated in each lesion partially or fully overlapping the optic radiations by a single experienced rater (O.A.), while blinded to OCT results captured by the certified ophthalmic technician.

Outcome measures: Primary outcome measures will be the correlation between absolute counts of CVS+ and/or PRLs, CVS percentage, and total T2 lesion volume in the post-geniculate visual pathway of each hemisphere with homonymous hemimacular GCIPL thickness at baseline, rates of GCIPL thinning over time, as well as rTSD index values. Exploratory outcome measures will include examining DTI measures (fractional anisotropy, radial diffusivity) within lesions and in the normal appearing white matter of the optic radiations with rTSD OCT metrics, as well as the correlation of CVS+/PRLs with deeper retinal layer (INL and ONL) atrophy.

Aim 2: Investigate the impact of retrograde trans-synaptic degeneration on visual function.

Visual dysfunction is common in MS and has been reported to occur similarly in pwMS with or without a history of optic neuritis (ON), suggesting mechanistic factors other than optic nerve inflammation contributing to visual dysfunction, such as rTSD. Visual loss is also a prominent cause of patient-reported quality-of-life reduction in MS, highlighting its importance in clinical monitoring. Posterior visual pathway lesions in MS have been associated with a wide range of visual symptomatology, including sudden onset hemianopsia, vague visual blurring in one or both eyes, or can present with a slow decline in vision over several months. However, longitudinal investigations linking severity of visual symptoms and progression of hemifield defects to specific post-geniculate lesion subtypes in MS have been lacking. This study will be the first to characterize the impact of MS lesion subtypes and rTSD in driving clinically meaningful longitudinal visual field defect progression.

Hypothesis: CVS+ and/or PRLs in the post-geniculate visual pathway associated with worse rTSD measures will exhibit worse contralateral hemifield visual defects on perimetry at baseline (compared to CVS−/PRL lesions and/or normal rTSD index), and higher risk of progression of hemifield defects over follow-up.

Experimental Design: Comprehensive visual function measures will be obtained on an annual basis (using equipment already available in the Visual Outcomes Laboratory and ophthalmic technician support) and will include: (1) best-corrected visual acuity in log MAR format, (2) low contrast letter acuity using SLOAN 2.5% and 1.25% charts, and (3) full-field standard automated perimetry. One drawback to standard or low contrast visual acuity measures is lack of hemifield specificity and accurate localization to lesional patterns within one hemisphere. Therefore, the primary visual outcomes analysis will focus on visual field (VF) defect measures obtained using an Octopus 600 perimetry device and performed with the pathology-based G-pattern protocol. The G-pattern protocol is designed to test locations following retinal nerve fiber layer bundles and GCIPL projections, which is germane to the analysis as it provides a direct VF correlate corresponding to GCIPL quadrant thickness, rTSD index, and posterior visual pathway lesional patterns. Two strategies will be compared to detect visual hemifield deterioration over time in pwMS: (1) hemifield mean defect (MD) analysis (averaged across both eyes), (2) spatial cluster-trend analysis of the pointwise VF defect values, which is more sensitive in detection of functional change in glaucoma but has not been investigated in pwMS to-date. VF studies with greater than 20% fixation losses, false positive or negative catch trials will be considered unreliable and excluded. Patient reported outcomes (NEI—Visual Function Questionnaire) will be obtained annually and correlated with rTSD indices, lesional subtypes on MRI, and visual function measures.

Aim 3: Assess whether rTSD of the visual pathway is linked to accelerated global brain and cervical spinal cord neurodegeneration, and disability progression independent of relapse activity.

Disability progression independent of relapse activity (PIRA) is thought to be mediated by the neurodegenerative components of MS and has been shown to start at the earliest stages in both relapsing and progressive subtypes, but subsequently evolves to be the main driver of cumulative disability accumulation in the progressive phase of the disease. Importantly, while PIRA is a key contributor to long-term disability accumulation in pwMS, it is poorly mitigated by traditional disease modifying therapies, which target mostly the inflammatory components of the disease. Therefore, there is a significant unmet need for the development of imaging biomarkers capable of identifying patients at risk of PIRA as well as targeted preventive or mitigation strategies. The presence of rTSD in the visual pathway of pwMS might indicate a higher susceptibility to TSD by lesions in other functional systems outside the visual pathway or a higher propensity for neuronal loss in general. It will be assessed whether pwMS with evidence of rTSD of the visual pathway exhibit faster rates of whole brain, cortical/subcortical gray matter, or spinal cord atrophy, as well as disability progression independent of relapses or new T2/enhancing lesions on MRI.

Hypothesis: PwMS who have higher rTSD index values of the visual pathway will exhibit accelerated whole brain, gray matter and spinal cord neurodegeneration, and higher risk of PIRA during follow-up.

Experimental Design: Annual 3T brain MRIs will be obtained, as detailed under Aim 1, and use this imaging data to simultaneously perform detailed computation of whole brain, cortical/subcortical gray matter, and white matter volumes using the Multi Atlas Cortical Reconstruction Using Implicit Surface Evolution (MA-CRUISE) method. Cervical spinal cord cross-sectional area will be measured using whole brain 3D T1 MPRAGE images, which also cover the upper cervical spinal cord. Standardized clinical disability measures will be collected on research participants during the standard of care clinical visits, including Expanded Disability Status Scale (EDSS), timed 25-foot walk (T25FW), 9-hole peg test (9HPT) scores, and Symbol Digit Modalities Test (SDMT). Confirmed disability worsening (CDW) will be defined as: (1) an increase in EDSS ($\geq 1.5$ points for patients with baseline EDSS of zero, $\geq 1.0$ point for patients with a baseline EDSS of 1-5, and by 0.5 points for patients with a baseline EDSS of $\geq 5.5$), 91 OR (2)$\geq 20\%$ worsening in T25FW, 9HPT, or SDMT scores. The primary outcome measure will be the incidence of PIRA between subjects with rTSD in the anterior visual pathway and those without rTSD, adjusting for demographic variables, total optic radiation T2 lesion volume, CVS+ and PRL lesion counts. Secondary outcome measures will include examining the rate of whole brain, cortical gray matter, thalamic and cross-sectional spinal cord atrophy between cases with rTSD and no evidence of rTSD using similar adjustments and an rTSD cut-off of +4. Given the sample size, these will be exploratory analyses with the hopes of using this preliminary data as a basis to expand the size of the cohort and validate whether rTSD in the visual pathway can serve as a biomarker of individual propensity for trans-synaptic degeneration, correlates with global neurodegeneration, and/or is predictive of PIRA in a larger cohort of pwMS.

3.2 Statistical Analysis

All hypotheses will be two-sided and tested at a significance level of 0.05. Calculations will be performed using R-package, version 4.1.

Aim 1

Power Considerations: The primary hypothesis is whether longitudinal change in GCIP from baseline over a 4-year period is associated with the presence or absence of CVS+/PRL lesions at baseline. The change for other OCT measures of interest (pRNFL, INL, and ONL) will also be presented. The estimated standard deviations (SD) of the mean change for pRNFL, GCIP, INL, and ONL are 1.0, 0.7, 0.2, and 0.7 respectively. Table 1 provides estimates of the minimal detectable change in OCT measures assuming a sample size of 80 patients with a single retinal measure for each patient as a conservative scenario, and a prevalence varying from 20% to 50% of patients with at least one CVS+/PRL lesion. Power considerations were performed using a Bonferroni corrected significance level of 0.025 (0.05/2) accounting for two types of lesions with 80% power using a two-sample equal variance t-test.

TABLE 1

Estimated minimal detectable change in OCT measures for Aim 1, and visual hemifield mean deviation for Aim 2 as a function of prevalence of patients with at least one CVS+/PRL lesion in the post-genticulate visual pathway varying from 10% to 50%

| Aim | Endpoint | SD | 10% | 20% | 30% | 40% | 50% |
|---|---|---|---|---|---|---|---|
| 1 | pRNFL (μm/year) | 1.0 | 1.2 | 0.9 | 0.8 | 0.7 | 0.7 |
| | GCIPL (μm/year) | 0.7 | 0.8 | 0.6 | 0.5 | 0.5 | 0.5 |
| | INL (μm/year) | 0.2 | 0.2 | 0.2 | 0.2 | 0.1 | 0.1 |
| | ONL (μm/year) | 0.7 | 0.8 | 0.6 | 0.5 | 0.5 | 0.5 |
| 2 | Hemifield mean deviation (dB) | 2.8 | 3.3 | 2.5 | 2.2 | 2.0 | 2.0 |

Statistical Analysis: For each OCT measure and rTSD index, the generalized additive model will be used for location, scale, and shape (GAMLSS) framework to determine the longitudinal relationship between OCT measures at 12, 24, 36, and 48 months as response variable with its baseline value, MRI biomarkers (CVS+ percentage, CVS+ lesion number, PRL, and total T2 lesion volume), time and interaction between time and MRI biomarkers as covariates. Model diagnostics will be performed using residual plots. Nested random effects will be incorporated to describe repeated measures and within-subject inter-eye correlation.

Aim 2

Power Considerations: The primary hypothesis is whether the visual hemifield mean deviation is associated with (a) the presence of CVS+/PRL lesions at baseline in the corresponding optic radiation; (b) OCT measures (rTSD index, pRNFL, GCIP, INL, and ONL thickness). Based on the preliminary data, the estimated standard deviation of the visual field deviation values is 2.8 dB. Table 1 (above) above presents the minimal detectable difference in the visual field mean deviation values with the presence/absence of CVS+/PRL lesions at baseline, assuming a prevalence of patients with at least one CVS+/PRL varying from 20% to 50%. Power considerations were calculated based on a two-sample t-test with equal variance, with 80% power and a Bonferroni corrected significance level of 0.025 (0.05/2) for two types of lesions.

Statistical Analysis: The approach presented in Aim 1 will be followed using the GAMLSS framework to determine the relationship between visual field mean deviations across each hemifield averaged across nasal and temporal hemifields of both eyes at baseline, 12, 24, 36, and 48 months as response variable, OCT measures, CVS+/PRL lesions at baseline, time and interaction between time and OCT measures as covariates. Visual field deviations will be modeled considering the spatial correlation within retinal nerve five bundles. Several spatial correlation structures will be studied (Exponential, Gaussian, Matérn), and the optimal one will be selected based on Akaike Information Criteria.

Aim 3

Power Considerations: The primary hypothesis is the association between rTSD indices of the visual pathway and the risk of PIRA over a 4-year period. Based on recent analysis of large MS datasets, the incidence of PIRA ranged between 20-40% for RRMS and 60-80% for progressive MS. It is conservatively estimated observing an incidence of PIRA of 20% over a 4-year follow-up period. The estimated standard deviation of rTSD in the preliminary data is 3.09. Power considerations were calculated with 80% power and a significance level of 0.05 based on a Cox regression model. With a sample size of 80 patients, the minimal detectable hazard ratio is 1.25.

Statistical Analysis: Time-to-event analysis will be performed using the Cox proportional hazards regression to identify baseline factors associated with PIRA events during follow-up, including rTSD index (continuous) or rTSD presence/absence (using a ±4 cut-off based on preliminary data). Time-to-event is defined as the number of months from baseline to PIRA or censorship. The proportional hazard assumption will be assessed via the scaled Schoenfeld residuals and the goodness of fit test.

Generally, any of the methods disclosed herein can be implemented using a system having a control system with one or more processors, and a memory device storing machine-readable instructions. The control system can be coupled to the memory device, and methods can be implemented when the machine-readable instructions are executed by at least one of the processors of the control system. The methods can also be implemented using a computer program product (such as a non-transitory computer readable medium) comprising instructions that when executed by a computer, cause the computer to carry out the steps of the methods.

One or more elements or aspects or steps, or any portion(s) thereof, from one or more of any of claims below can be combined with one or more elements or aspects or steps, or any portion(s) thereof, from one or more of any of the other claims or combinations thereof, to form one or more additional implementations and/or claims of the present disclosure.

Alternative Implementations

Alternative Implementation 1. A method for quantifying retrograde trans-synaptic degeneration (rTSD) in a patient, the method comprising: receiving optical coherence tomography (OCT) image data associated with a left retina and a right retina of the patient; analyzing the OCT image data to determine a thickness of one or more retinal layers of the left retina and one or more retinal layers of the right retina; and based at least in part on the determined thicknesses, determining a value of an rTSD index that is indicative of a level of rTSD in the patient.

Alternative Implementation 2. The method of Alternative Implementation 1, wherein the value of the rTSD index relative to 0 is indicative of whether a cause of the rTSD is located in a left hemisphere of a brain of the patient or a right hemisphere of the brain of the patient.

Alternative Implementation 3. The method of Alternative Implementation 2, wherein the index value being greater than 0 indicates that a cause of the rTSD is located in a left hemisphere of a brain of the patient.

Alternative Implementation 4. The method of Alternative Implementation 2 or Alternative Implementation 3, wherein the index value being less than 0 indicates that a cause of the rTSD is located in a right hemisphere of a brain of the patient.

Alternative Implementation 5. The method of Alternative Implementation 3 or Alternative Implementation 4, wherein the cause of the rTSD is a lesion in a left optic radiation of the patient, a right optic radiation of the patient, or both.

Alternative Implementation 6. The method of Alternative Implementation 5, wherein the lesion is a paramagnetic rim lesion, a central vein sign+(CVS+) lesion, or both.

Alternative Implementation 7. The method of any one of Alternative Implementations 1 to 6, wherein an absolute value of the rTSD index is indicative of a magnitude of the rTSD in one hemisphere of a brain of the patient relative to an opposing hemisphere of the brain of the patient.

Alternative Implementation 8. The method of any one of Alternative Implementations 1 to 7, wherein the one or more retinal layers of the right retina include a right temporal ganglion cell and inner plexiform layer (right temporal GCIPL) and a right nasal GCIPL.

Alternative Implementation 9. The method of any one of Alternative Implementations 1 to 8, wherein the one or more retinal layers of the left retina include a left temporal GCIPL and a left nasal GCIPL.

Alternative Implementation 10. The method of any one of Alternative Implementations 1 to 9, wherein the rTSD index value is based at least in part on a ratio between (i) a combined thickness of one or more retinal layers located on a left side of the left retina and a left side of the right retina and (ii) a combined thickness of one or more retinal layers located on a right side of the right retina and a right side of the left retina patient.

Alternative Implementation 11. The method of Alternative Implementation 10, wherein the one or more retinal layers located on the left side of the left retina and the left side of the right retina includes a left temporal GCIPL and a right nasal GCIPL.

Alternative Implementation 12. The method of Alternative Implementation 10 or Alternative Implementation 11, wherein the one or more retinal layers located on the left side of the left retina and the left side of the right retina includes a left temporal GCIPL, a left temporal inner nuclear layer (INL), a left temporal outer nuclear layer (ONL), and a right nasal GCIPL.

Alternative Implementation 13. The method of any one of Alternative Implementations 10 to 12, wherein the one or more retinal layers located on the right side of the right retina and the right side of the left retina includes a right temporal GCIPL and a left nasal GCIPL.

Alternative Implementation 14. The method of any one of Alternative Implementations 10 to 13, wherein the one or more retinal layers located on the right side of the right retina and the right side of the left retina includes a right temporal GCIPL, a right temporal INL, a right temporal ONL, and a left nasal GCPL.

Alternative Implementation 15. The method of any one of Alternative Implementations 1 to 14, wherein the rTSD index value is based at least in part on a ratio between (i) a total thickness of one or more retinal layers connected to a left optic radiation of the patient, and (ii) a total thickness of one or more retinal layers connected to a right optic radiation of the patent.

Alternative Implementation 16. The method of Alternative Implementation 15, wherein the one or more retinal layers connected to the left optic radiation of the patient includes a left temporal GCIPL and a right nasal GCIPL.

Alternative Implementation 17. The method of Alternative Implementation 15 or Alternative Implementation 16, wherein the one or more retinal layers connected to the left optic radiation includes a left temporal GCIPL, a left temporal inner nuclear layer (INL), a left temporal outer nuclear layer (ONL), and a right nasal GCPL.

Alternative Implementation 18. The method of any one of Alternative Implementations 15 to 17, wherein the one or more retinal layers connected to the right optic radiation includes a right temporal GCIPL and a left nasal GCIPL.

Alternative Implementation 19. The method of any one of Alternative Implementations 15 to 18, wherein the one or more retinal layers connected to the right optic radiation includes a right temporal GCIPL, a right temporal INL, a right temporal ONL, and a left nasal GCPL.

Alternative Implementation 20. The method of any one of Alternative Implementations 1 to 19, wherein the rTSD index value is based at least in part on (i) a ratio between a thickness of a first retinal layer of the right retina and a second retina layer of the right retina, (ii) a ratio between a thickness of a first retinal layer of the left retina and a second retina layer of the left retina, or (iii) both (i) and (ii).

Alternative Implementation 21. The method of Alternative Implementation 20, wherein the first retinal layer of the right retina is a right nasal GCIPL and the second retinal layer of the right retina is a right temporal GCIPL.

Alternative Implementation 22. The method of Alternative Implementation 20 or Alternative Implementation 21, wherein the first retinal layer of the left retina is a left nasal GCIPL and the second retinal layer of the left retina is a left temporal GCIPL.

Alternative Implementation 23. The method of any one of Alternative Implementations 1 to 22, wherein the rTSD index value is based at least in part on (i) a ratio between a thickness of a first retinal layer connected to a left optic radiation of the patient and a first retina layer connected to a right optic radiation of the patient, (ii) a ratio between a thickness of a second retinal layer connected to a left optic radiation of the patient and a second retina layer connected to a right optic radiation of the patient, or (iii) both (i) and (ii).

Alternative Implementation 24. The method of Alternative Implementation 23, wherein the first retinal layer connected to the left optic radiation is a right nasal GCIPL and the first retinal layer connected to the right optic radiation is a right temporal GCIPL.

Alternative Implementation 25. The method of Alternative Implementation 23 or Alternative Implementation 24, wherein the second retinal layer connected to the left optic radiation is a left temporal GCIPL and the second retinal layer connected to the right optic radiation is a left nasal GCIPL.

Alternative Implementation 26. The method of any one of Alternative Implementations 1 to 25, wherein the rTSD index is given by $\text{rTSD}_{index}$=((left temporal thickness+right nasal GCIPL thickness)/(right temporal thickness+left nasal GCIP thickness)−1)×100.

Alternative Implementation 27. The method of any one of Alternative Implementations 1 to 26, wherein the rTSD index is given by $\text{rTSD}_{index}$=((((right nasal GCIPL thickness)/(right temporal GCIPL thickness)+(left temporal GCIPL thickness)/(left nasal GCIPL thickness))×1/2)−1)×100.

Alternative Implementation 28. The method of any one of Alternative Implementations 1 to 27, wherein an absolute value of the rTSD index is indicative of a severity of hemimacular ganglion cell atrophy in at least one hemisphere of a brain of the patient.

Alternative Implementation 29. The method of any one of Alternative Implementations 1 to 28, wherein analyzing the OCT image data includes segmenting the left retina and the right retina within the OCT image data to identify the one or more retinal layers of the left retina and the one or more retinal layers of the right retina.

Alternative Implementation 30. The method of any one of Alternative Implementations 1 to 29, wherein the value of the rTSD index is indicative of a level of dysfunction in a visual field of the patient.

Alternative Implementation 31. The method of any one of Alternative Implementations 1 to 30, wherein the value of the rTSD index being greater than or equal to 3, or less than or equal to −3, is associated with the patient having multiple sclerosis (MS).

Alternative Implementation 32. A system for quantifying retrograde trans-synaptic degeneration (rTSD) in a patient, the system comprising: a memory device having stored thereon machine-readable instructions; and a control system including one or more processors configured to execute the machine-readable instructions to implement the method of any one of Alternative Implementations 1 to 31.

Alternative Implementation 33. A system for quantifying retrograde trans-synaptic degeneration (rTSD) in a patient, the system comprising a control system configured to implement the method of any one of Alternative Implementations 1 to 31.

Alternative Implementation 34. A computer program product comprising instructions which, when executed by a computer, cause the computer to carry out the method of any one of Alternative Implementations 1 to 31.

Alternative Implementation 35. The computer program product of Alternative Implementation 34, wherein the computer program product is a non-transitory computer readable medium.

Alternative Implementation 36. A system for quantifying retrograde trans-synaptic degeneration (rTSD) in a patient, the system comprising: a memory device having stored thereon machine-readable instructions; and a control system including one or more processors configured to execute the machine-readable instructions to cause the control system to: receive optical coherence tomography (OCT) image data associated with a left retina and a right retina of the patient; analyze the OCT image data to determine a thickness of one or more retinal layers of the left retina and one or more retinal layers of the right retina; and based at least in part on the determined thicknesses, determine a value of an rTSD index that is indicative of a level of rTSD in the patient.

Alternative Implementation 37. The system of Alternative Implementation 36, further comprising an OCT imaging system configured to generate the OCT image data.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations or alternative implementations according to aspects of the present disclosure may combine any number of features from any of the implementations described herein, such as, for example, in the alternative implementations described above.

What is claimed is:

1. A method for quantifying retrograde trans-synaptic degeneration (rTSD) in a patient, the method comprising:

receiving optical coherence tomography (OCT) image data associated with a left retina and a right retina of the patient;

analyzing the OCT image data to determine a thickness of one or more retinal layers of the left retina and one or more retinal layers of the right retina; and

20 based at least in part on the determined thicknesses, determining a value of an rTSD index that is indicative of a level of rTSD in the patient, the rTSD index value being based on a ratio between (i) a combined thickness of one or more retinal layers of the left retina connected to a left optic radiation of the patient and one or more retinal layers of the right retina connected to the left optic radiation of the patient, and (ii) a combined thickness of one or more retinal layers of the left retina connected to a right optic radiation of the patient and one or more retinal layers of the right retina connected to the right optic radiation of the patient.

2. The method of claim 1, wherein a cause of the rTSD is a lesion in the left optic radiation of the patient, the right optic radiation of the patient, or both.

3. The method of claim 2, wherein the lesion is a paramagnetic rim lesion, a central vein sign+(CVS+)lesion, or both.

4. The method of claim 1, wherein an absolute value of the rTSD index is indicative of a magnitude of the rTSD in one hemisphere of a brain of the patient relative to an opposing hemisphere of the brain of the patient.

5. The method of claim 1, wherein:

the one or more retinal layers of the left retina connected to the left optic radiation of the patent includes a left temporal ganglion cell and inner plexiform layer (right temporal GCIPL);

the one or more retinal layers of the right retina connected to the left optic radiation of the patient includes a right nasal GCIPL;

the one or more retinal layers of the left retina connected to the right optic radiation of the patient includes a left nasal GCIPL; and the one or more retinal layers of the right retina connected to the right optic radiation of the patient a right temporal GCIPL.

6. The method of claim 5, wherein the rTSD index is given by $$rTSD_{index} = \left( \frac{\text{left temporal } GCIPL \text{ thickness} + \text{right nasal } GCIPL \text{ thickness}}{\text{right temporal } GCIPL \text{ thickness} + \text{left nasal } GCIP \text{ thickness}} - 1 \right) \times 100.$$

7. The method of claim 6, wherein the value of the rTSD index relative to 0 is indicative of whether a cause of the rTSD is located in a left hemisphere of a brain of the patient or a right hemisphere of the brain of the patient.

8. The method of claim 7, wherein the index value being greater than 0 indicates that a cause of the rTSD is located in a left hemisphere of a brain of the patient, and wherein the index value being less than 0 indicates that a cause of the rTSD is located in a right hemisphere of a brain of the patient.

9. The method of claim 1, wherein the one or more retinal layers connected to the left optic radiation of the patient includes one or more retinal layers located on a left side of the left retina and a left side of the right retina, and wherein the one or more retinal layers connected to the right optic radiation of the patient includes one or more retinal layers located on a right side of the right retina and a right side of the left retina.

10. The method of claim 1, wherein analyzing the OCT image data includes segmenting the left retina and the right retina within the OCT image data to identify the one or more retinal layers of the left retina and the one or more retinal layers of the right retina.

11. The method of claim 1, wherein:

the one or more retinal layers of the right retina connected to the left optic radiation of the patient includes a right nasal temporal ganglion cell and inner plexiform layer (right temporal GCIPL);

the one or more retinal layers of the right retina connected to the right optic radiation of the patient includes a right temporal GCIPL;

the one or more retinal layers of the left retina connected to the left optic radiation of the patient includes a left temporal GCIPL; and the one or more retinal layers of the left retina connected to the right optic radiation of the patient a left nasal GCIPL.

12. The method of claim 11, wherein the one or more retinal layers connected to the left optic radiation of the patient includes one or more retinal layers located on a left side of the left retina and a left side of the right retina, and wherein the one or more retinal layers connected to the right optic radiation of the patient includes one or more retinal layers located on a right side of the right retina and a right side of the left retina.

13. The method of claim 11, wherein the rTSD index is given by $rTSD_{index} =$ $$rTSD_{index} = \left( \left( \left( \frac{\text{right nasal } GCIPL \text{ thickness}}{\text{right temporal } GCIPL \text{ thickness}} + \frac{\text{left temporal } GCIPL \text{ thickness}}{\text{left nasal } GCIPL \text{ thickness}} \right) \times \frac{1}{2} \right) - 1 \right) \times 100.$$

14. The method of claim 13, wherein the value of the rTSD index relative to 0 is indicative of whether a cause of the rTSD is located in a left hemisphere of a brain of the patient or a right hemisphere of the brain of the patient.

15. The method of claim 14, wherein the index value being greater than 0 indicates that a cause of the rTSD is located in a left hemisphere of a brain of the patient, and wherein the index value being less than 0 indicates that a cause of the rTSD is located in a right hemisphere of a brain of the patient.

16. The method of claim 11, wherein a cause of the rTSD is a lesion in the left optic radiation of the patient, the right optic radiation of the patient, or both.

17. The method of claim 16, wherein the lesion is a paramagnetic rim lesion, a central vein sign+(CVS+) lesion, or both.

18. The method of claim 11, wherein an absolute value of the rTSD index is indicative of a magnitude of the rTSD in one hemisphere of a brain of the patient relative to an opposing hemisphere of the brain of the patient.

19. The method of claim 11, wherein analyzing the OCT image data includes segmenting the left retina and the right retina within the OCT image data to identify the one or more retinal layers of the left retina and the one or more retinal layers of the right retina.

20. A method for quantifying retrograde trans-synaptic degeneration (rTSD) in a patient, the method comprising:

receiving optical coherence tomography (OCT) image data associated with a left retina and a right retina of the patient;

analyzing the OCT image data to determine a thickness of one or more retinal layers of the left retina and one or more retinal layers of the right retina; and based at least in part on the determined thicknesses, determining a value of an rTSD index that is indicative of a level of rTSD in the patient, the rTSD index value being based on a sum of (i) a ratio between a thickness of one or more retinal layers of the right retina connected to a left optic radiation of the patient and one or more retinal layers of the right retina connected to a right optic radiation of the patient and (ii) a ratio between a thickness of one or more retinal layers of the left retina connected to the left optic radiation of the patient and one or more retinal layers of the left retina connected to the right optic radiation of the patient.

* * * * *